US00PP28326P3

(12) United States Plant Patent
Kleinwee

(10) Patent No.: US PP28,326 P3
(45) Date of Patent: Aug. 22, 2017

(54) ***PETUNIA* PLANT NAMED 'PEHY0018'**

(50) Latin Name: *Petunia hybrida*
Varietal Denomination: PEHY0018

(71) Applicant: SYNGENTA PARTICIPATIONS AG, Basel (CH)

(72) Inventor: Theodorus Cornelis Maria van Kleinwee, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/999,981

(22) Filed: Jul. 21, 2016

(65) Prior Publication Data

US 2017/0064894 P1 Mar. 2, 2017

(51) Int. Cl.
*A01H 5/02* (2006.01)

(52) U.S. Cl.
USPC ..... Plt./356.19

(58) Field of Classification Search
USPC ..... Plt./356.19, 356.16
CPC ..... A01H 5/02
See application file for complete search history.

*Primary Examiner* — Kent L Bell
(74) *Attorney, Agent, or Firm* — Dale Skalla

(57) ABSTRACT

A new *Petunia* plant named 'PEHY0018' particularly distinguished by its medium sized, light blue colored flowers with a strong pattern of dark veining, rather dark green foliage, good branching, early flowering, and an upright growing habit.

1 Drawing Sheet

Latin name of the genus and species of the plant claimed: *Petunia hybrida.*

Varietal denomination: 'PEHY0018'.

BACKGROUND OF THE NEW PLANT

The present invention comprises a new *Petunia*, botanically known as *Petunia hybrida*, and hereinafter referred to by the variety name 'PEHY0018'.

'PEHY0018' is a product of a planned breeding program. The new cultivar has medium sized, light blue colored flowers with a strong pattern of dark veining, rather dark green foliage, good branching, early flowering, and has an upright growing habit.

'PEHY0018' originated from a hybridization made in October 2010 in a controlled breeding environment in Enkhuizen, The Netherlands. The female parent was the unpatented proprietary plant designated 'N0047-4' with light blue to almost white flower color with medium strong veining and an upright growth habit.

The male parent of 'PEHY0018' was 'Petlibluve', U.S. Plant Pat. No. 19,227, with a trailing, outwardly spreading and mounded plant habit, freely branching habit, freely flowering habit, single flowers that are very light blue in color with dark veins, and good garden performance.

The resulting seeds were sown in January 2011. 'PEHY0018' was selected as one flowering plant within the progeny of the stated cross in May 2011 in a controlled environment in Enkhuizen, The Netherlands.

The first act of asexual reproduction of 'PEHY0018' was accomplished when vegetative cuttings were propagated from the initial selection in June 2016 in a controlled environment in Enkhuizen, The Netherlands.

BRIEF SUMMARY OF INVENTION

Horticultural examination of plants grown from cuttings of the plant initiated in June 2011, and continuing thereafter, has demonstrated that the combination of characteristics as herein disclosed for 'PEHY0018' are firmly fixed and are retained through successive generations of asexual reproduction.

'PEHY0018' has not been observed under all possible environmental conditions. The phenotype may vary significantly with variations in environment such as temperature, light intensity, and day length.

A Plant Breeder's Rights for this cultivar was applied for in the European Union on Sep. 2, 2015 and assigned application number 2015/2040. 'PEHY0018' has not been made publicly available prior to the effective filing date of this application, notwithstanding any disclosure that may have been made less than one year prior to the effective filing date of this application by the inventor or another who obtained 'PEHY0018' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawings show typical flower and foliage characteristics of 'PEHY0018' with colors being as true as possible with an illustration of this type.

Figure 1:
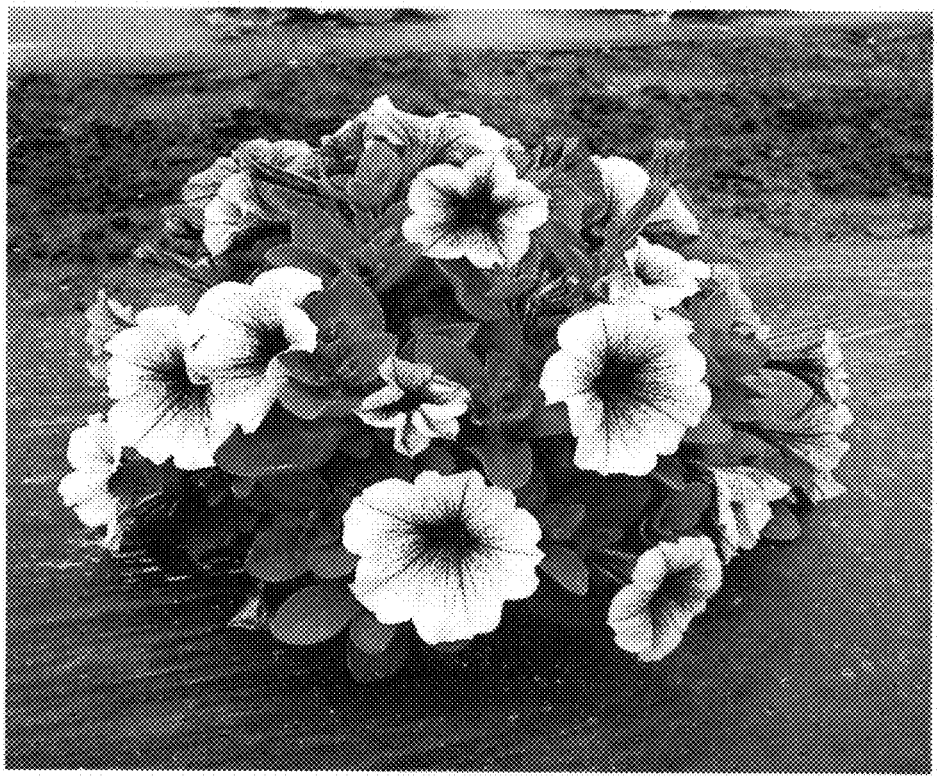
Figure 2:
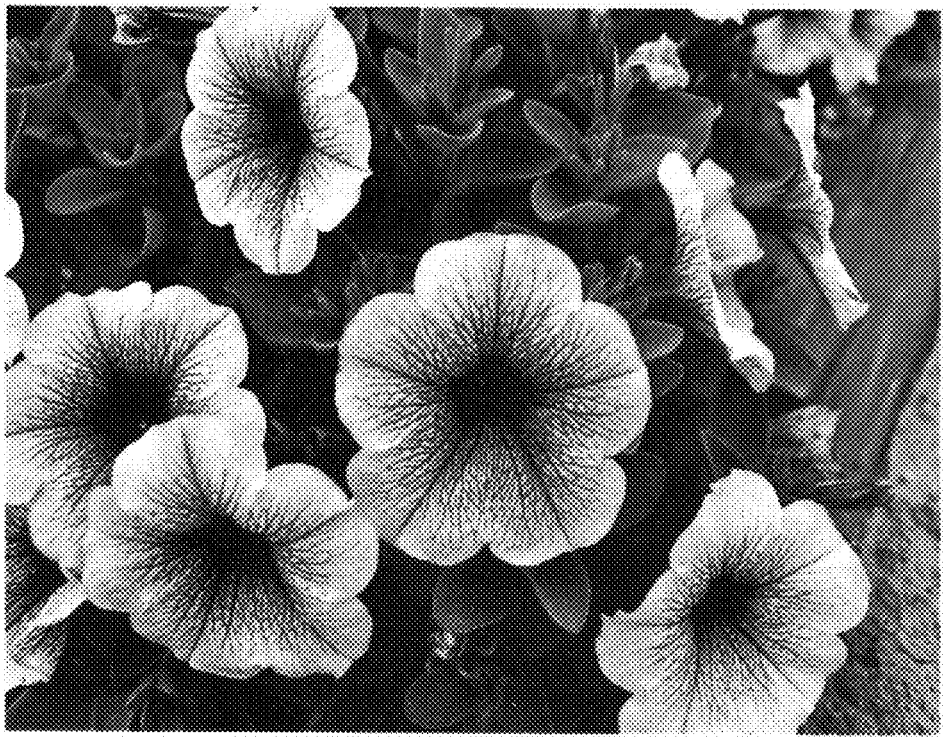

The photographic drawings show in FIG. 1. a flowering plant of the new variety and in FIG. 2. a close-up of the flowers.

DETAILED BOTANICAL DESCRIPTION

The aforementioned photographs were taken in July 2015 from plants growing in a field trial in Enkhuizen, The Netherlands. These plants were approximately 17 weeks of age.

The plant descriptions and measurements were taken in June 2016 in Andijk, Netherlands on 16 week old plants that were growing in big containers outdoors.

Color references are made to The Royal Horticultural Society Colour Chart (R.H.S.) 2001.

TABLE 1

DIFFERENCES BETWEEN THE NEW VARIETY 'PEHY0018' AND A SIMILAR VARIETY

| | 'PEHY0018' | 'Petlibluve' |
|---|---|---|
| Flower color: | Light blue | Light blue |
| Flower vein color: | Dark blue | Dark blue |
| Flowering response: | Fairly early | Late |
| Reaction to cold conditions in spring: | Tolerant | When exposed to night temperatures below 3 degrees C., necrosis on leaves will occur |
| Vigor: | Medium | Strong |
| Habit: | Upright | Trailing |

Plant:

*Form, growth and habit.*—Upright, freely branching.
*Plant height.*—17 cm.
*Plant height (inflorescence included).*—21 cm.
*Plant diameter (width).*—25 cm.

Roots:

*Number of days to initiate and produce roots.*—16 to 20 days at about 22 degrees C.
*Type.*—Fine, fibrous, free branching.
*Color.*—RHS N155D.

Foliage:

*Arrangement.*—Alternate, simple.
*Immature leaf, color upper surface.*—RHS 137B.
*Immature leaf, color lower surface.*—RHS 137C.
*Mature leaf, color upper surface.*—RHS 137A.
*Mature leaf, color lower surface.*—RHS 137C.
*Length.*—4.6-5.4 cm.
*Width.*—1.5-2.8 cm.
*Shape.*—Elliptical to ovate.
*Base shape.*—Attenuate.
*Apex shape.*—Acute.
*Margin.*—Entire.
*Texture, upper surface.*—Densely covered with short glandular hair of variable length.
*Lower surface.*—Densely covered with short hair.
*Color of veins, upper surface.*—Darker than RHS 143A.
*Color of veins, lower surface.*—RHS 143A.
*Petiole color.*—RHS 143A.
*Length.*—0.3-0.4 cm.
*Diameter.*—0.3 cm.
*Petiole texture.*—Short glandular hair.

Stem:

*Quantity of main branches per plant.*—16.
*Color of stem.*—RHS 146B.
*Length of stem.*—17 cm.
*Diameter.*—0.3 cm.
*Length of internodes.*—1.5-2.5 cm.
*Texture.*—Dense, mostly glandular hairs.
*Color of pedicel.*—RHS 146A, little RHS 177B anthocyanin just below the bud or inflorescence.
*Length of pedicel.*—2.0-3.0 cm.
*Diameter of pedicel.*—0.20 cm.
*Texture of pedicel.*—Densely covered with short glandular hairs.

Inflorescence:

*Type.*—Flowers solitary in upper leaf axis; flowers variable in orientation.
*Floret type.*—Funnel-shaped; 5 lobed petals; fused at the base.
*Blooming habit.*—Continuous flowering throughout the summer months, little affected by heat.
*Quantity of inflorescences per plant.*—Approximately 10.
*Lastingness of individual blooms on the plant.*—About 9 days.
*Fragrance.*—None.

Bud (just when opening):

*Color.*—RHS 83A, much lighter than RHS 83A towards top.
*Length.*—4.0-4.5 cm.
*Width.*—0.9-1.1 cm.
*Shape.*—Tridentate.

Immature inflorescence:

*Flower horizontal diameter.*—5.5 cm.
*Color petals, upper surface.*—RHS 82D, veins RHS 83A.
*Color petals, lower surface.*—RHS 82D, veins darker than RHS N83A.

Mature flower:

*Flower horizontal diameter.*—6.0 cm.
*Flower height (vertical).*—4.5 cm.
*Color upper surface.*—RHS 82D to somewhat lighter than RHS 82D, veins RHS 83A.
*Color lower surface.*—RHS 82D, veins darker than RHS N83A.
*All petals.*—
*Apex shape.*—Truncate to slightly cuspidate.
*Margin.*—Entire.
*Waviness of margin.*—Weak.
*Petal lobation.*—Weak to medium.
*Petal texture, upper surface.*—Papillose, glabrous.
*Petal texture, lower surface.*—Papillose.
*Corolla tube color outside.*—RHS 83A to almost black, RHS N202A.
*Corolla tube color inside.*—Almost black, RHS N202A.
*Corolla tube length.*—3.0 cm.
*Corolla tube texture, outside.*—Pilose, glandular hairs.
*Corolla tube texture, inside.*—Glabrous.

Calyx:

*Color of sepal, upper surface.*—RHS 137A.
*Color of sepal, lower surface.*—RHS 137A.
*Length.*—1.8 cm.
*Width.*—0.3 cm.
*Shape.*—Ensiform.
*Apex shape.*—Acute.
*Base.*—Fused.
*Margins.*—Entire.
*Texture, upper surface.*—Densely covered with short glandular hairs.
*Lower surface.*—Covered with short glandular hairs.

Reproductive organs:

*Pistil.*—1.
*Length.*—2.3 cm.
*Style color.*—RHS 143D, some anthocyanin RHS 177A towards top.
*Style length.*—1.8 cm.
*Stigma color.*—RHS 143A.

*Stamens.*—

*Quantity per flower.*—5.

*Color of filaments.*—RHS 155B, some anthocyanin RHS 177A at base.

*Length filaments.*—1.9 cm.

*Anther color.*—RHS 202C.

*Anther length.*—0.2 cm.

*Anther shape.*—Elliptical.

*Color of pollen.*—RHS 202D.

*Pollen amount.*—Moderate.

*Fertility/seed set.*—Has not been observed on this hybrid.

*Disease/pest resistance.*—Has not been observed on this hybrid.

What is claimed is:

1. A new and distinct variety of *Petunia* plant named 'PEHY0018' substantially as illustrated and described herein.

* * * * *